(12) United States Patent
Hu et al.

(10) Patent No.: US 6,531,309 B1
(45) Date of Patent: Mar. 11, 2003

(54) HUMAN TRANSPORTER PROTEINS AND POLYNUCLEOTIDES ENCODING THE SAME

(75) Inventors: Yi Hu, The Woodlands, TX (US); James Alvin Kieke, Houston, TX (US); Brian Zambrowicz, The Woodlands, TX (US); Jean-Pierre Revelli, Spring, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/795,927

(22) Filed: Feb. 28, 2001

Related U.S. Application Data
(60) Provisional application No. 60/185,956, filed on Feb. 29, 2000.

(51) Int. Cl.[7] .................. C07H 21/04; C12N 15/63; C12N 1/21; C12N 1/15; C12N 15/85; C12N 15/86

(52) U.S. Cl. ................ 435/252.3; 435/320.1; 435/254.11; 435/254.2; 435/325; 536/23.5

(58) Field of Search ................ 536/23.5, 23.4, 536/23.2, 23.1; 530/350; 435/320.1, 325, 252.3, 254.11, 254.2

(56) References Cited

U.S. PATENT DOCUMENTS

| | | |
|---|---|---|
| 4,215,051 A | 7/1980 | Schroeder et al. |
| 4,376,110 A | 3/1983 | David et al. |
| 4,594,595 A | 6/1986 | Struckman |
| 4,631,211 A | 12/1986 | Houghten |
| 4,689,405 A | 8/1987 | Frank et al. |
| 4,713,326 A | 12/1987 | Dattagupta et al. |
| 4,946,778 A | 8/1990 | Ladner et al. |
| 5,198,344 A | 3/1993 | Croop et al. |
| 5,252,743 A | 10/1993 | Barrett et al. |
| 5,424,186 A | 6/1995 | Fodor et al. |
| 5,445,934 A | 8/1995 | Fodor et al. |
| 5,459,127 A | 10/1995 | Felgner et al. |
| 5,556,752 A | 9/1996 | Lockhart et al. |
| 5,658,782 A | 8/1997 | Amara et al. |
| 5,700,637 A | 12/1997 | Southern |
| 5,744,305 A | 4/1998 | Fodor et al. |
| 5,837,458 A | 11/1998 | Minshull et al. |
| 5,866,699 A | 2/1999 | Smyth |
| 5,869,336 A | 2/1999 | Meyer et al. |
| 5,877,397 A | 3/1999 | Lonberg et al. |
| 5,948,767 A | 9/1999 | Scheule et al. |
| 6,075,181 A | 6/2000 | Kucherlapati et al. |
| 6,110,490 A | 8/2000 | Thierry |
| 6,150,584 A | 11/2000 | Kucherlapati et al. |

FOREIGN PATENT DOCUMENTS

| | | |
|---|---|---|
| JP | 11-146790 | 6/1999 |
| WO | WO 90/06047 A2 | 6/1990 |
| WO | WO 98/44954 A1 | 10/1998 |
| WO | WO 98/55858 A1 | 12/1998 |

OTHER PUBLICATIONS

Lohi et al, Mapping of five new putative anion transporter genes in human and characterization of SLC26A6, a candidate gene for pancreatic anion exchanger. Genomics 70:102–112, 2000.*

Peer Bork and Eugene V. Koonin, Predicting functions from protein sequences—where are the bottlenecks? Nature Genetics 18:313–318,1998.*

Ji et al, G–protein–coupled receptors, J. Biol. Chem, 273:17299–17302, 1998.*

Bird et al, 1988, "Single–Chain Antigen–Binding Proteins", Science 242:423–426.

Bitter et al, 1987, "Expression and Secretion Vectors for Yeast", Methods in Enzymology 153:516–544.

Colbere–Garapin et al, 1981, "A New Dominant Hybrid Selective Marker for Higher Eukaryotic Cells", J. Mol. Biol. 150:1–14.

Gautier et al, 1987, "α–DNA IV:α–anomeric and β–anomeric tetrathymidylates covalently linked to intercalating oxazolopyridocarbazole. Synthesis, physiochemical properties and poly (rA) binding", Nucleic Acids Research 15(16):6625–6641.

Greenspan et al, 1993, "Idiotypes: structure and immunogenicity", FASEB Journal 7:437–444.

Huse et al, 1989, "Generation of a Large Combinatorial Library of the Immunoglobulin Repertoire in Phage Lambda", Science 246:1275–1281.

Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.

Inoue et al, 1987, "Sequence–dependent hydrolysis of RNA using modified oligonucleotide splints and R Nase H", FEBS Letters 215(2):327–330.

Inoue et al, 1987, "Synthesis and hybridization studies on two complementary nona(2'O–methyl)ribonucleotides", Nucleic Acids Research 15(15):6131–6149.

Inouye & Inouye, 1985, "Up–promoter mutations in the lpp gene of *Escherichia coli*", Nucleic Acids Research 13(9):3101–3110.

Janknecht et al, 1991, "Rapid and efficient purification of native histidine–tagged protein expressed by recombinant vaccinia virus", PNAS 88:8972–8976.

Kohler & Milstein, 1975, "Continuous cultures of fused cells secreting antibody of predefined specificity", Nature 256:495–497.

Logan et al, 1984, "Adenovirus tripartite leader sequence enhances translation of mRNAs late after infection", Proc. Natl. Acad. Sci. USA 81:3655–3659.

(List continued on next page.)

*Primary Examiner*—Elizabeth Kemmerer
*Assistant Examiner*—Ruixiang Li

(57) ABSTRACT

Novel human polynucleotide and polypeptide sequences are disclosed that can be used in therapeutic, diagnostic, and pharmacogenomic applications.

4 Claims, No Drawings

OTHER PUBLICATIONS

Lowy et al, 1980, "Isolation of Transforming DNA: Cloning the Hamster aprt Gene", Cell 22:817–823.

Morrison et al, 1984, "Chimeric human antibody molecules: Mouse antigen–binding domains with human constant region domains", Proc. Natl. Acad. Sci. USA 81:6851–6855.

Mulligan & Berg, 1981, "Selection for animal cells that express the *Escherichia coli* gene coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Applications", J. of Immunology 147:2429–2438.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the *Autographa californica* Nuclear Polyhedrosis Virus Genome: Deletion Mutations within the Polyhedrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV. DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable domains secreted from *Escherichia coli*", Nature 341:544–546.

Wigler et al, 1977, "Transfer of Purified Herpes Virus Thymidine Kinase Gene to Cultured Mouse Cells", Cell 11:223–232.

Japanese Abstract, JP 11–146790, XP002177829.

Nagase et al., "Prediction of the Coding Sequences of Unidentified Human Genes, XIII. The Complete Sequences of 100 New cDNA Clones from Brain Which Code for Large Proteins in vitro," DNA Research, Universal Academy Press, JP, vol. 6, 1999, pp. 63–70, XP000952912.

Database EMBL Sequence Database (online), Hinxton, UK, Apr. 9, 1999, O'Hara et al., "*Homo sapiens* mRNA for KIAA0956 Protein, Partial cds.," XP002177825; EMBL:AB023173; abstract.

Halleck et al., "Differential Expression of Putative Transbilayer Amphipath Transporters," Physiological Genomics, vol. 1, 1999, pp. 139–150, XP002177823.

Database EMBL Sequence Database (Online), Hinxton, UK; Nov. 24, 2999, Halleck et al., "*Homo sapiens* putative E1–E2 ATPase mRNA, partial cds," XP002177826, EMBL:AF15648; abstract.

Database EMBL Sequence Database (Online), Hinxton, UK; Nov. 17, 1999, Bloecker et al., "*Homo sapiens* mRNA; cDNA DKFZp434N1615 (from clone DKFZp434N1615); partial cds," XP002177827; EMBL:HSM801332, Accession No. AL133061; abstract.

Database EMBL Sequence Database (Online), Hinxton, UK; Mar. 12, 1999, Ottenwaelder et al., "*Homo sapiens* EST DKFZp434J238_r1 (from clone DKFZp434J238_r1) EST partial cds," XP002177828, EMBL:HSM011423, Accession No. AL046573; abstract.

McMahon et al., "Mammalian Zinc Transporters," Journal of Nutrition, vol. 128, No. 4, Apr. 1998, pp. 667–670, XP002177824; ISSN: 0022–3166.

International Search Report, International Application No. PCT/US01/06462, Sep. 26, 2001 (Attorney Docket No. LEX–0141–PCT).

* cited by examiner

SEQUENCE LISTING

<160> NUMBER OF SEQ ID NOS: 11

<210> SEQ ID NO 1
<211> LENGTH: 3534
<212> TYPE: DNA
<213> ORGANISM: homo sapiens

<400> SEQUENCE: 1

```
atgtggcgct ggatccggca gcagctgggt tttgacccac cacatcagag tgacacaaga      60
accatctacg tagccaacag gtttcctcag aatggccttt acacacctca gaaatttata     120
gataacagga tcatttcatc taagtacact gtgtggaatt ttgttccaaa aaatttattt     180
gaacagttca gaagagtggc aaacttttat tttcttatta tatttttggt tcagcttatg     240
attgatacac ctaccagtcc agttaccagt ggacttccat tattctttgt gataacagta     300
actgccataa agcagggata tgaagattgg ttacggcata actcagataa tgaagtaaat     360
ggagctcctg tttatgttgt tcgaagtggt ggccttgtaa aaactagatc aaaaaacatt     420
cgggtgggtg atattgttcg aatagccaaa gatgaaattt ttcctgcaga cttggtgctt     480
ctgtcctcag atcgactgga tggttcctgt cacgttacaa ctgctagttt ggacggagaa     540
actaacctga agacacatgt ggcagttcca gaaacagcat tattacaaac agttgccaat     600
ttggacactc tagtagctgt aatagaatgc agcaaccag aagcagactt atacagattc     660
atgggacgaa tgatcataac ccaacaaatg gaagaaattg taagacctct ggggccggag     720
agtctcctgc ttcgtggagc cagattaaaa aacacaaaag aaatttttgg tgttgcggta     780
tacactggaa tggaaactaa gatggcatta aattacaaga gcaaatcaca gaaacgatct     840
gcagtagaaa agtcaatgaa tacatttttg ataatttatc tagtaattct tatatctgaa     900
gctgtcatca gcactatctt gaagtataca tggcaagctg aagaaaaatg ggatgaacct     960
tggtataacc aaaaaacaga acatcaaaga aatagcagta agattctgag atttatttca    1020
gacttccttg ctttttggt tctctacaat ttcatcattc caatttcatt atatgtgaca    1080
gtcgaaatgc agaaatttct tggatcattt tttattggct gggatcttga tctgtatcat    1140
```

-continued

```
gaagaatcag atcagaaagc tcaagtcaat acttccgatc tgaatgaaga gcttggacag    1200
gtagagtacg tgtttacaga taaaactggt acactgacag aaaatgagat gcagtttcgg    1260
gaatgttcaa ttaatggcat gaaataccaa gaaattaatg gtagacttgt acccgaagga    1320
ccaacaccag actcttcaga aggaaactta tcttatctta gtagtttatc ccatcttaac    1380
aacttatccc atcttacaac cagttcctct ttcagaacca gtcctgaaaa tgaaactgaa    1440
ctaattaaag aacatgatct cttctttaaa gcagtcagtc tctgtcacac tgtacagatt    1500
agcaatgttc aaactgactg cactggtgat ggtccctggc aatccaacct ggcaccatcg    1560
cagttggagt actatgcatc ttcaccagat gaaaaggctc tagtagaagc tgctgcaagg    1620
attggtattg tgtttattgg caattctgaa gaaactatgg aggttaaaac tcttggaaaa    1680
ctggaacggt acaaactgct tcatattctg gaatttgatt cagatcgtag gagaatgagt    1740
gtaattgttc aggcaccttc aggtgagaag ttattatttg ctaaaggagc tgagtcatca    1800
attctcccta aatgtatagg tggagaaata gaaaaaacca gaattcatgt agatgaattt    1860
gctttgaaag ggctaagaac tctgtgtata gcatatagaa aatttacatc aaaagagtat    1920
gaggaaatag ataaacgcat atttgaagcc aggactgcct tgcagcagcg ggaagagaaa    1980
ttggcagctg ttttccagtt catagagaaa gacctgatat tacttggagc cacagcagta    2040
gaagacagac tacaagataa agttcgagaa actattgaag cattgagaat ggctggtatc    2100
aaagtatggg tacttactgg ggataaacat gaaacagctg ttagtgtgag tttatcatgt    2160
ggccattttc atagaaccat gaacatcctt gaacttataa accagaaatc agacagcgag    2220
tgtgctgaac aattgaggca gcttgccaga agaattacag aggatcatgt gattcagcat    2280
gggctggtag tggatgggac cagcctatct cttgcactca gggagcatga aaaactattt    2340
atggaagttt gcagaaattg ttcagctgta ttatgctgtc gtatggctcc actgcagaaa    2400 gcaaagtaa taagactaat aaaaatatca cctgagaaac ctataacatt ggctgttggt    2460
gatggtgcta atgacgtaag catgatacaa gaagcccatg ttggcatagg aatcatgggt    2520
aaagaaggaa gacaggctgc aagaaacagt gactatgcaa tagccagatt taagttcctc    2580
tccaaattgc ttttttgttca tggtcatttt tattatatta gaatagctac ccttgtacag    2640
tatttttttt ataagaatgt gtgctttatc acaccccagt ttttatatca gttctactgt    2700
ttgttttctc agcaaacatt gtatgacagc gtgtacctga ctttatacaa tatttgtttt    2760
acttccctac ctattctgat atatagtctt ttggaacagc atgtagaccc tcatgtgtta    2820
caaaataagc ccacccttta tcgagacatt agtaaaaacc gcctcttaag tattaaaaca    2880
tttctttatt ggaccatcct gggcttcagt catgccttta ttttcttttt tggatccctat    2940 ttactaatag ggaaagatac atctctgctt ggaaatggcc agatgttygg aaactggaca    3000
tttggcactt tggtcttcac agtcatggtt attacagtca cagtaaagat ggctctggaa    3060
actcattttt ggacttggat caaccatctc gttacctggg gatctattat attttatttt    3120 gtatttcct tgttttatgg agggattctc tggccatttt tgggctccca gaatatgtat    3180
tttgtgttta ttcagctcct gtcaagtggt tctgcttggt ttgccataat cctcatggtt    3240
gttacatgtc tatttcttga tatcataaag aaggtctttg accgacacct ccaccctaca    3300
agtactgaaa aggcacagct tactgaaaca aatgcaggta tcaagtgctt ggactccatg    3360
tgctgtttcc cggaaggaga agcagcgtgt gcatctgttg gaagaatgct ggaacgagtt    3420
ataggaagat gtagtccaac ccacatcagc agatcatgga gtgcatcgga tccttctat    3480 accaacgaca ggagcatctt gactctctcc acaatggact catctacttg ttaa           3534
```

```
<210> SEQ ID NO 2
<211> LENGTH: 1177
<212> TYPE: PRT
<213> ORGANISM: homo sapiens

<400> SEQUENCE: 2

Met Trp Arg Trp Ile Arg Gln Gln Leu Gly Phe Asp Pro Pro His Gln
 1               5                  10                  15

Ser Asp Thr Arg Thr Ile Tyr Val Ala Asn Arg Phe Pro Gln Asn Gly
             20                  25                  30

Leu Tyr Thr Pro Gln Lys Phe Ile Asp Asn Arg Ile Ile Ser Ser Lys
         35                  40                  45

Tyr Thr Val Trp Asn Phe Val Pro Lys Asn Leu Phe Glu Gln Phe Arg
 50                  55                  60

Arg Val Ala Asn Phe Tyr Phe Leu Ile Ile Phe Leu Val Gln Leu Met
65                  70                  75                  80

Ile Asp Thr Pro Thr Ser Pro Val Thr Ser Gly Leu Pro Leu Phe Phe
                 85                  90                  95

Val Ile Thr Val Thr Ala Ile Lys Gln Gly Tyr Glu Asp Trp Leu Arg
            100                 105                 110

His Asn Ser Asp Asn Glu Val Asn Gly Ala Pro Val Tyr Val Val Arg
        115                 120                 125

Ser Gly Gly Leu Val Lys Thr Arg Ser Lys Asn Ile Arg Val Gly Asp
    130                 135                 140

Ile Val Arg Ile Ala Lys Asp Glu Ile Phe Pro Ala Asp Leu Val Leu
145                 150                 155                 160

Leu Ser Ser Asp Arg Leu Asp Gly Ser Cys His Val Thr Thr Ala Ser
                165                 170                 175

Leu Asp Gly Glu Thr Asn Leu Lys Thr His Val Ala Val Pro Glu Thr
            180                 185                 190

Ala Leu Leu Gln Thr Val Ala Asn Leu Asp Thr Leu Val Ala Val Ile
        195                 200                 205

Glu Cys Gln Gln Pro Glu Ala Asp Leu Tyr Arg Phe Met Gly Arg Met
    210                 215                 220

Ile Ile Thr Gln Gln Met Glu Glu Ile Val Arg Pro Leu Gly Pro Glu
225                 230                 235                 240

Ser Leu Leu Leu Arg Gly Ala Arg Leu Lys Asn Thr Lys Glu Ile Phe
                245                 250                 255

Gly Val Ala Val Tyr Thr Gly Met Glu Thr Lys Met Ala Leu Asn Tyr
            260                 265                 270

Lys Ser Lys Ser Gln Lys Arg Ser Ala Val Glu Lys Ser Met Asn Thr
        275                 280                 285

Phe Leu Ile Ile Tyr Leu Val Ile Leu Ser Glu Ala Val Ile Ser
        290                 295                 300

Thr Ile Leu Lys Tyr Thr Trp Gln Ala Glu Glu Lys Trp Asp Glu Pro
305                 310                 315                 320

Trp Tyr Asn Gln Lys Thr Glu His Gln Arg Asn Ser Ser Lys Ile Leu
                325                 330                 335

Arg Phe Ile Ser Asp Phe Leu Ala Phe Leu Val Leu Tyr Asn Phe Ile
            340                 345                 350

Ile Pro Ile Ser Leu Tyr Val Thr Val Glu Met Gln Lys Phe Leu Gly
        355                 360                 365

Ser Phe Phe Ile Gly Trp Asp Leu Asp Leu Tyr His Glu Glu Ser Asp
```

-continued

```
              370              375              380
Gln Lys Ala Gln Val Asn Thr Ser Asp Leu Asn Glu Glu Leu Gly Gln
385              390              395              400
Val Glu Tyr Val Phe Thr Asp Lys Thr Gly Thr Leu Thr Glu Asn Glu
             405              410              415
Met Gln Phe Arg Glu Cys Ser Ile Asn Gly Met Lys Tyr Gln Glu Ile
             420              425              430
Asn Gly Arg Leu Val Pro Glu Gly Pro Thr Pro Asp Ser Ser Glu Gly
             435              440              445
Asn Leu Ser Tyr Leu Ser Ser Leu Ser His Leu Asn Asn Leu Ser His
             450              455              460
Leu Thr Thr Ser Ser Phe Arg Thr Ser Pro Glu Asn Glu Thr Glu
465              470              475              480
Leu Ile Lys Glu His Asp Leu Phe Phe Lys Ala Val Ser Leu Cys His
                 485              490              495
Thr Val Gln Ile Ser Asn Val Gln Thr Asp Cys Thr Gly Asp Gly Pro
             500              505              510
Trp Gln Ser Asn Leu Ala Pro Ser Gln Leu Glu Tyr Tyr Ala Ser Ser
             515              520              525
Pro Asp Glu Lys Ala Leu Val Glu Ala Ala Arg Ile Gly Ile Val
530              535              540
Phe Ile Gly Asn Ser Glu Glu Thr Met Glu Val Lys Thr Leu Gly Lys
545              550              555              560
Leu Glu Arg Tyr Lys Leu Leu His Ile Leu Glu Phe Asp Ser Asp Arg
             565              570              575
Arg Arg Met Ser Val Ile Val Gln Ala Pro Ser Gly Glu Lys Leu Leu
             580              585              590
Phe Ala Lys Gly Ala Glu Ser Ser Ile Leu Pro Lys Cys Ile Gly Gly
             595              600              605
Glu Ile Glu Lys Thr Arg Ile His Val Asp Glu Phe Ala Leu Lys Gly
610              615              620
Leu Arg Thr Leu Cys Ile Ala Tyr Arg Lys Phe Thr Ser Lys Glu Tyr
625              630              635              640
Glu Glu Ile Asp Lys Arg Ile Phe Glu Ala Arg Thr Ala Leu Gln Gln
             645              650              655
Arg Glu Glu Lys Leu Ala Ala Val Phe Gln Phe Ile Glu Lys Asp Leu
             660              665              670
Ile Leu Leu Gly Ala Thr Ala Val Glu Asp Arg Leu Gln Asp Lys Val
             675              680              685
Arg Glu Thr Ile Glu Ala Leu Arg Met Ala Gly Ile Lys Val Trp Val
             690              695              700
Leu Thr Gly Asp Lys His Glu Thr Ala Val Ser Val Ser Leu Ser Cys
705              710              715              720
Gly His Phe His Arg Thr Met Asn Ile Leu Glu Leu Ile Asn Gln Lys
             725              730              735
Ser Asp Ser Glu Cys Ala Glu Gln Leu Arg Gln Leu Ala Arg Arg Ile
             740              745              750
Thr Glu Asp His Val Ile Gln His Gly Leu Val Val Asp Gly Thr Ser
             755              760              765
Leu Ser Leu Ala Leu Arg Glu His Glu Lys Leu Phe Met Glu Val Cys
             770              775              780
Arg Asn Cys Ser Ala Val Leu Cys Cys Arg Met Ala Pro Leu Gln Lys
785              790              795              800
```

-continued

Ala Lys Val Ile Arg Leu Ile Lys Ile Ser Pro Glu Lys Pro Ile Thr
            805                 810                 815
Leu Ala Val Gly Asp Gly Ala Asn Asp Val Ser Met Ile Gln Glu Ala
            820                 825                 830
His Val Gly Ile Gly Ile Met Gly Lys Glu Gly Arg Gln Ala Ala Arg
            835                 840                 845
Asn Ser Asp Tyr Ala Ile Ala Arg Phe Lys Phe Leu Ser Lys Leu Leu
        850                 855                 860
Phe Val His Gly His Phe Tyr Tyr Ile Arg Ile Ala Thr Leu Val Gln
865                 870                 875                 880
Tyr Phe Phe Tyr Lys Asn Val Cys Phe Ile Thr Pro Gln Phe Leu Tyr
                885                 890                 895
Gln Phe Tyr Cys Leu Phe Ser Gln Gln Thr Leu Tyr Asp Ser Val Tyr
            900                 905                 910
Leu Thr Leu Tyr Asn Ile Cys Phe Thr Ser Leu Pro Ile Leu Ile Tyr
            915                 920                 925
Ser Leu Leu Glu Gln His Val Asp Pro His Val Leu Gln Asn Lys Pro
        930                 935                 940
Thr Leu Tyr Arg Asp Ile Ser Lys Asn Arg Leu Leu Ser Ile Lys Thr
945                 950                 955                 960
Phe Leu Tyr Trp Thr Ile Leu Gly Phe Ser His Ala Phe Ile Phe Phe
                965                 970                 975
Phe Gly Ser Tyr Leu Leu Ile Gly Lys Asp Thr Ser Leu Leu Gly Asn
            980                 985                 990
Gly Gln Met Phe Gly Asn Trp Thr Phe Gly Thr Leu Val Phe Thr Val
            995                 1000                1005
Met Val Ile Thr Val Thr Val Lys Met Ala Leu Glu Thr His Phe Trp
        1010                1015                1020
Thr Trp Ile Asn His Leu Val Thr Trp Gly Ser Ile Ile Phe Tyr Phe
1025                1030                1035                1040
Val Phe Ser Leu Phe Tyr Gly Gly Ile Leu Trp Pro Phe Leu Gly Ser
                1045                1050                1055
Gln Asn Met Tyr Phe Val Phe Ile Gln Leu Leu Ser Ser Gly Ser Ala
            1060                1065                1070
Trp Phe Ala Ile Ile Leu Met Val Val Thr Cys Leu Phe Leu Asp Ile
            1075                1080                1085
Ile Lys Lys Val Phe Asp Arg His Leu His Pro Thr Ser Thr Glu Lys
        1090                1095                1100
Ala Gln Leu Thr Glu Thr Asn Ala Gly Ile Lys Cys Leu Asp Ser Met
1105                1110                1115                1120
Cys Cys Phe Pro Glu Gly Glu Ala Ala Cys Ala Ser Val Gly Arg Met
                1125                1130                1135
Leu Glu Arg Val Ile Gly Arg Cys Ser Pro Thr His Ile Ser Arg Ser
            1140                1145                1150
Trp Ser Ala Ser Asp Pro Phe Tyr Thr Asn Asp Arg Ser Ile Leu Thr
            1155                1160                1165
Leu Ser Thr Met Asp Ser Ser Thr Cys
        1170                1175

<210> SEQ ID NO 3
<211> LENGTH: 1125
<212> TYPE: DNA
<213> ORGANISM: homo sapiens -continued

```
<400> SEQUENCE: 3
atgtggcgct ggatccggca gcagctgggt tttgacccac cacatcagag tgacacaaga      60
accatctacg tagccaacag gtttcctcag aatggccttt acacacctca gaaatttata    120
gataacagga tcatttcatc taagtacact gtgtggaatt ttgttccaaa aaatttattt    180
gaacagttca gaagagtggc aaactttat tttcttatta tattttttggt tcagcttatg    240 attgatacac ctaccagtcc agttaccagt ggacttccat tattctttgt gataacagta    300
actgccataa agcagggata tgaagattgg ttacggcata actcagataa tgaagtaaat    360
ggagctcctg tttatgttgt tcgaagtggt ggccttgtaa aaactagatc aaaaaacatt    420
cgggtgggtg atattgttcg aatagccaaa gatgaaattt tcctgcaga cttggtgctt     480 ctgtcctcag atcgactgga tggttcctgt cacgttacaa ctgctagttt ggacggagaa    540
actaacctga agacacatgt ggcagttcca gaaacagcat tattacaaac agttgccaat    600
ttggacactc tagtagctgt aatagaatgc agcaaccag aagcagactt atacagattc     660
atgggacgaa tgatcataac ccaacaaatg gaagaaattg taagacctct ggggccggag    720
agtctcctgc ttcgtggagc cagattaaaa aacacaaag aaattttggt tgttgcggta     780
tacactggaa tggaaactaa gatggcatta aattacaaga gcaaatcaca gaaacgatct    840
gcagtagaaa agtcaatgaa tacattttg ataatttatc tagtaattct tatatctgaa     900
gctgtcatca gcactatctt gaagtataca tggcaagctg aagaaaaatg ggatgaacct    960
tggtataacc aaaaaacaga acatcaaaga aatagcaatt ctgagattta tttcagactt   1020
ccttgctttt ttggttctct acaatttcat cattccaatt tcattatatg tgacagtcga   1080
aatgcagaaa tttcttggat catttttat tggctgggat cttga                    1125
```

<210> SEQ ID NO 4
<211> LENGTH: 374
<212> TYPE: PRT
<213> ORGANISM: homo sapiens

<400> SEQUENCE: 4

```
Met Trp Arg Trp Ile Arg Gln Gln Leu Gly Phe Asp Pro Pro His Gln
 1               5                  10                  15

Ser Asp Thr Arg Thr Ile Tyr Val Ala Asn Arg Phe Pro Gln Asn Gly
            20                  25                  30

Leu Tyr Thr Pro Gln Lys Phe Ile Asp Asn Arg Ile Ile Ser Ser Lys
        35                  40                  45

Tyr Thr Val Trp Asn Phe Val Pro Lys Asn Leu Phe Glu Gln Phe Arg
    50                  55                  60

Arg Val Ala Asn Phe Tyr Phe Leu Ile Ile Phe Leu Val Gln Leu Met
65                  70                  75                  80

Ile Asp Thr Pro Thr Ser Pro Val Thr Ser Gly Leu Pro Leu Phe Phe
                85                  90                  95

Val Ile Thr Val Thr Ala Ile Lys Gln Gly Tyr Glu Asp Trp Leu Arg
            100                 105                 110

His Asn Ser Asp Asn Glu Val Asn Gly Ala Pro Val Tyr Val Val Arg
        115                 120                 125

Ser Gly Gly Leu Val Lys Thr Arg Ser Lys Asn Ile Arg Val Gly Asp
    130                 135                 140

Ile Val Arg Ile Ala Lys Asp Glu Ile Phe Pro Ala Asp Leu Val Leu
145                 150                 155                 160

Leu Ser Ser Asp Arg Leu Asp Gly Ser Cys His Val Thr Thr Ala Ser
```

-continued

```
                    165                 170                 175
Leu Asp Gly Glu Thr Asn Leu Lys Thr His Val Ala Val Pro Glu Thr
                180                 185                 190
Ala Leu Leu Gln Thr Val Ala Asn Leu Asp Thr Leu Val Ala Val Ile
            195                 200                 205
Glu Cys Gln Gln Pro Glu Ala Asp Leu Tyr Arg Phe Met Gly Arg Met
    210                 215                 220
Ile Ile Thr Gln Gln Met Glu Glu Ile Val Arg Pro Leu Gly Pro Glu
225                 230                 235                 240
Ser Leu Leu Leu Arg Gly Ala Arg Leu Lys Asn Thr Lys Glu Ile Phe
                245                 250                 255
Gly Val Ala Val Tyr Thr Gly Met Glu Thr Lys Met Ala Leu Asn Tyr
            260                 265                 270
Lys Ser Lys Ser Gln Lys Arg Ser Ala Val Glu Lys Ser Met Asn Thr
        275                 280                 285
Phe Leu Ile Ile Tyr Leu Val Ile Leu Ile Ser Glu Ala Val Ile Ser
    290                 295                 300
Thr Ile Leu Lys Tyr Thr Trp Gln Ala Glu Glu Lys Trp Asp Glu Pro
305                 310                 315                 320
Trp Tyr Asn Gln Lys Thr Glu His Gln Arg Asn Ser Asn Ser Glu Ile
                325                 330                 335
Tyr Phe Arg Leu Pro Cys Phe Phe Gly Ser Leu Gln Phe His His Ser
            340                 345                 350
Asn Phe Ile Ile Cys Asp Ser Arg Asn Ala Glu Ile Ser Trp Ile Ile
        355                 360                 365
Phe Tyr Trp Leu Gly Ser
    370

<210> SEQ ID NO 5
<211> LENGTH: 7277
<212> TYPE: DNA
<213> ORGANISM: homo sapiens

<400> SEQUENCE: 5
gccgcgggat gggaacgcgg cgcggggagt gaggcagtgg cggcggcggc ggtaagcgga      60
acttcggccc gagggctcg  cccgctcccg cctctgtctt gtcggcctcc acctgcagcc     120
ccgcggcccc cgcgccccgc gggacccgga cggcgacgac gggggaatgt ggcgctggat     180
ccggcagcag ctgggttttg acccaccaca tcagagtgac acaagaacca tctacgtagc     240
caacaggttt cctcagaatg cctttacac  acctcagaaa tttatagata acaggatcat     300
ttcatctaag tacactgtgt ggaattttgt tccaaaaaat ttatttgaac agttcagaag     360
agtggcaaac tttttatttc ttattatatt tttggttcag cttatgattg atacacctac     420
cagtccagtt accagtggac ttccattatt ctttgtgata acagtaactg ccataaagca     480
gggatatgaa gattggttac ggcataactc agataatgaa gtaaatggag ctcctgttta     540
tgttgttcga agtggtggcc ttgtaaaaac tagatcaaaa acattcgggt gggtgatat     600 tgttcgaata gccaaagatg aaattttttcc tgcagacttg gtgcttctgt cctcagatcg     660
actggatggt tcctgtcacg ttacaactgc tagtttggac ggagaaacta acctgaagac     720
acatgtggca gttccagaaa cagcattatt acaaacagtt gccaatttgg acactctagt     780
agctgtaata gaatgccagc aaccagaagc agacttatac agattcatgg gacgaatgat     840
cataacccaa caaatggaag aaattgtaag acctctgggg ccggagagtc tcctgcttcg     900
```

-continued

```
tggagccaga ttaaaaaaca caaaagaaat ttttggtgtt gcggtataca ctggaatgga      960
aactaagatg gcattaaatt acaagagcaa atcacagaaa cgatctgcag tagaaaagtc     1020
aatgaataca ttttttgataa tttatctagt aattcttata tctgaagctg tcatcagcac   1080
tatcttgaag tatacatggc aagctgaaga aaaatgggat gaaccttggt ataaccaaaa    1140
aacagaacat caaagaaata gcagtaagat tctgagattt atttcagact tccttgcttt    1200
tttggttctc tacaatttca tcattccaat ttcattatat gtgacagtcg aaatgcagaa    1260
atttcttgga tcatttttta ttggctggga tcttgatctg tatcatgaag aatcagatca    1320
gaaagctcaa gtcaatactt ccgatctgaa tgaagagctt ggacaggtag agtacgtgtt    1380
tacagataaa actggtacac tgacagaaaa tgagatgcag tttcgggaat gttcaattaa    1440
tggcatgaaa taccaagaaa ttaatggtag acttgtaccc gaaggaccaa caccagactc    1500
ttcagaagga aacttatctt atcttagtag tttatcccat cttaacaact tatcccatct    1560
tacaaccagt tcctctttca gaaccagtcc tgaaaatgaa actgaactaa ttaaagaaca    1620
tgatctcttc tttaaagcag tcagtctctg tcacactgta cagattagca atgttcaaac    1680
tgactgcact ggtgatggtc cctggcaatc caacctggca ccatcgcagt ggagtacta    1740 tgcatcttca ccagatgaaa aggctctagt agaagctgct gcaaggattg gtattgtgtt    1800
tattggcaat tctgaagaaa ctatggaggt taaaactctt ggaaaactgg aacggtacaa    1860
actgcttcat attctggaat tgattcaga tcgtaggaga atgagtgtaa ttgttcaggc     1920
accttcaggt gagaagttat tatttgctaa aggagctgag tcatcaattc tccctaaatg    1980
tataggtgga gaaatagaaa aaaccagaat tcatgtagat gaatttgctt tgaaagggct    2040
aagaactctg tgtatagcat atagaaaatt tacatcaaaa gagtatgagg aaatagataa    2100
acgcatattt gaagccagga ctgccttgca gcagcgggaa gagaaattgg cagctgtttt    2160
ccagttcata gagaaagacc tgatattact tggagccaca gcagtagaag acagactaca    2220
agataaagtt cgagaaacta ttgaagcatt gagaatggct ggtatcaaag tatgggtact    2280
tactggggat aaacatgaaa cagctgttag tgtgagtttta tcatgtggcc attttcatag   2340
aaccatgaac atccttgaac ttataaacca gaaatcagac agcgagtgtg ctgaacaatt    2400
gaggcagctt gccagaagaa ttacagagga tcatgtgatt cagcatgggc tggtagtgga    2460
tgggaccagc ctatctcttg cactcaggga gcatgaaaaa ctatttatgg aagtttgcag    2520
aaattgttca gctgtattat gctgtcgtat ggctccactg cagaaagcaa agtaataag    2580 actaataaaa atatcacctg agaaacctat aacattggct gttggtgatg gtgctaatga    2640
cgtaagcatg atacaagaag cccatgttgg cataggaatc atgggtaaag aaggaagaca    2700
ggctgcaaga aacagtgact atgcaatagc cagatttaag ttcctctcca aattgctttt    2760
tgttcatggt cattttatt atattagaat agctacccttt gtacagtatt ttttttataa    2820
gaatgtgtgc tttatcacac cccagttttt atatcagttc tactgtttgt tttctcagca    2880
aacattgtat gacagcgtgt acctgacttt atacaatatt tgttttactt ccctaccctat   2940 tctgatatat agtcttttgg aacagcatgt agaccctcat gtgttacaaa ataagcccac    3000
cctttatcga gacattagta aaaaccgcct cttaagtatt aaaacatttc tttattggac    3060
catcctgggc ttcagtcatg ccttttatttt cttttttgga tcctatttac taataggaa    3120 agatacatct ctgcttggaa atggccagat gttyggaaac tggacatttg gcactttggt    3180
cttcacagtc atggttatta cagtcacagt aaagatggct ctggaaactc attttttggac  3240 ttggatcaac catctcgtta cctggggatc tattatatttt tattttgtat tttccttgtt   3300
```

-continued

```
ttatggaggg attctctggc cattttggg ctcccagaat atgtattttg tgtttattca      3360
gctcctgtca agtggttctg cttggtttgc cataatcctc atggttgtta catgtctatt      3420
tcttgatatc ataaagaagg tctttgaccg acacctccac cctacaagta ctgaaaaggc      3480
acagcttact gaaacaaatg caggtatcaa gtgcttggac tccatgtgct gtttcccgga      3540
aggagaagca gcgtgtgcat ctgttggaag aatgctggaa cgagttatag aagatgtag       3600 tccaacccac atcagcagat catggagtgc atcggatcct ttctatacca acgacaggag      3660
catcttgact ctctccacaa tggactcatc tacttgttaa aggggcagta gtactttgtg      3720
ggagccagtt cacctccttt cctaaaattc agtgtgatca ccctgttaat ggccacacta      3780
gctctgaaat taatttccaa aatctttgta gtagttcata cccactcaga gttataatgg      3840
caaacaaaca gaaagcatta gtacaagccc ctcccaacac ccttaatttg aatctgaaca      3900
tgttaaaatt tgagaataaa gagacatttt tcatctcttt gtctggtttg tcccttgtgc      3960
ttatgggact cctaatggca tttcagtctg ttgctgaggc cattatattt taatataaat      4020
gtagaaaaaa gagagaaatc ttagtaaaga gtatttttta gtattagctt gattattgac      4080
tcttctattt aaatctgctt ctgtaaatta tgctgaaagt ttgccttgag aactctattt      4140
ttttattaga gttatattta aagcttttca tgggaaaagt taatgtgaat actgaggaat      4200
tttggtccct cagtgacctg tgttgttaat tcattaatgc attctgagtt cacagagcaa      4260
attaggagaa tcatttccaa ccattattta ctgcagtatg gggagtaaat ttataccaat      4320
tcctctaact gtactgtaac acagcctgta aagttagcca tataaatgca agggtatatc      4380
atatatacaa atcaggaatc aggtccgttc accgaacttc aaattgatgt ttactaatat      4440
ttttgtgaca gagtataaag accctatagt gggtaaatta gatactatta gcatattatt      4500
aatttaatgt ctttatcatt ggatcttttg catgctttaa tctggttaac atatttaaat      4560
ttgctttttt tctctttacc tgaaggctct gtgtatagta tttcatgaca tcgttgtaca      4620
gtttaactat atcaataaaa agtttggaca gtatttaaat attgcaaata tgtttaatta      4680
tacaaatcag aatagtatgg gtaattaaat gaatacaaaa agaagagcct ctttctgcag      4740
ccgacttaga catgctcttc cctttctata agctagattt tagaataaag ggtttcagtt      4800
aataatctta ttttcaggtt atgtcatcta acttatagca aactaccaca atacagtgag      4860
ttctgccagt gtcccagtac aaggcatatt tcaggtgtgg ctgtggaatg taaaaatgct      4920
caacttgtat caggtaatgt tagcaataaa ttaaatgcta agaatgatta atcgggtaca      4980
tgttactgta attaactcat tgcacttcaa aacctaactt ccatcctgaa tttatcaagt      5040
agttcagtat tgtcatttgt ttttgtttta ttgaaagta atgttgtctt aagatttaga       5100
agtgattatt agcttgagaa ctattaccca gctctaagca aataatgatt gtatacatat      5160
taagataatg gttaaatgcg gttttaccaa gttttccctt gaaaatgtaa ttcctttatg      5220
gagatttatt gtgcagccct aagcttcctt cccatttcat gaatataagg cttctagaat      5280
tggactggca ggggaaagaa tggtagagac agaaattaag actttatcct tgtttgcttg      5340
taaactatta ttttcttgct aatgtaacat ttgtctgttc cagtgatgta aggatattaa      5400
gttattaagc taaatattaa ttttcaaaaa tagtccttct ttaacttaga tatttcatag      5460
ctggatttag gaagatctgt tattctggaa gtactaaaaa gaataataca acgtacaatg      5520
tctgcattca ctaattcatg ttccagaaga ggaaataatg aagatatact cagtagagta      5580
ctaggtggga ggatatggaa atttgctcat aaaatctctt ataaacgtg catataacaa       5640
```

```
aatgacaccc agtaggcctg cattacattt acatgaccgt gtttatttgc catcaaataa    5700
actgagtact gacaccagac aaagactcca aagtcataaa atagcctatg accaactgca    5760
gcaagacagg aggtcagctc gcctataatg gtgcttaaag tgtgattgat gtaattttct    5820
gtactcacca tttgaagtta gttaaggaga actttatttt tttaaaaaaa gtaaatggca    5880
accactagtg tgctcatcct gaactgttac tccaaatcca ctccgttttt aaagcaaaat    5940
tatcttgtga ttttaagaaa agagttttct atttatttaa gaaagtaaca atgcagtctg    6000
caagctttca gtagttttct agtgctatat tcatcctgta aaactcttac tacgtaacca    6060
gtaatcacaa ggaaagtgtc ccctttgcat atttctttaa aattctttct ttggaaagta    6120
tgatgttgat aattaactta cccttatctg ccaaaaccag agcaaaatgc taaatacgtt    6180
attgctaatc agtggtctca aatcgatttg cctcccttttg cctcgtctga gggctgtaag    6240
cctgaagata gtggcaagca ccaagtcagt ttccaaaatt gcccctcagc tgctttaagt    6300
gactcagcac cctgcctcag cttcagcagg cstaggctca ccctgggcgg agcaaagtat    6360
gggccaggga gaactacagc tacgaagacc tgctgtcgag ttgagaaaag gggagaattt    6420
atggtctgaa ttttctaact gtcctctttc ttgggtctaa agctcataat acacaaaggc    6480
ttccagacct gagccacacc caggccctat cctgaacagg agactaaaca gaggcaaatc    6540
aaccctagga aatacttgca ttctgcccta cggttagtac caggactgag gtcatttcta    6600
ctggaaaaga ttgtgagatt gaacttatct gatcgcttga gactcctaat aggcaggagt    6660
caaggccact agaaaattga cagttaagag ccaaagtttt taaaatatg ctactctgaa    6720 aaatctcgtg aaggctgtag gaaaagggag aatcttccat gttggtgttt ttcctgtaaa    6780
gatcagtttg gggtatgata taagcaggta ttaataaaaa taacacacca aagagttacg    6840
taaaacatgt tttattaatt ttggtcccca cgtacagaca ttttatttct attttgaaat    6900
gagttatcta ttttcataaa agtaaaacac tattaaagtg ctgttttatg tgaaataact    6960
tgaatgttgt tcctataaaa aatagatcat aactcatgat atgtttgtaa tcatggtaat    7020 ttagatttt atgaggaatg agtatctgga aatattgtag caatacttgg tttaaaattt    7080
tggacctgag acactgtggc tgtctaatgt aatcctttaa aaattctctg cattgtcagt    7140
aaatgtagta tattattgta cagctactca taattttta agtttatga agttatattt    7200 atcaaataaa aactttccta tataattaaa aaaaaaaaa aaaaaaaaa aaaaacaaa    7260 aaaaaaaaaa aaaaaaa                                                  7277

<210> SEQ ID NO 6
<211> LENGTH: 2913
<212> TYPE: DNA
<213> ORGANISM: homo sapiens

<400> SEQUENCE: 6
atggcacaac tagagaggag cgccatctct ggcttcagct ctaagtccag gcgaaactca      60
ttcgcatatg atgttaagcg tgaagtatac aatgaggaga cctttcaaca ggaacacaaa     120
aggaaggcct cctcttctgg gaacatgaac atcaacatca ccaccttcag acaccacgtc     180
cagtgccgct gctcatggca caggttccta cgatgcrtgc ttacaatctt tcccttccta     240
gaatggatgt gtatgtatcg attaaaggat tggcttctgg gagacttact tgctggtata     300
agtgttggcc ttgtgcaagt tccccaaggc ctgacactta gtttgctggc aaggcaactg     360
attcctcctc tcaacatcgc ttatgcagct ttctgttctt cggtaatcta tgtaattttt     420
ggatcgtgtc atcaaatgtc cgttggttcc ttcttcctgg tgagtgctct gctgatcaac     480
```

```
gttctgaaag tgagcccatt caacaacggt caactggtca tgggatcttt cgtcaagaat     540
gagttttcgg cccctccta ccttatgggc tataataaat ccttgagtgt ggtggcaacc     600 acaactttc tgactgggat tattcagcta ataatgggcg tattgggttt gggcttcatt     660
gccacttacc ttccggagtc tgcaatgaat gcttacctgg ctgctgtggc acttcatatc    720
atgctgtccc agctgacttt catctttggg attatgatta gtttccatgc cggtcccatc    780
tccttcttct atgacataat taattactgt gtagctctcc caaaagcgaa ttccaccagc    840
attctagtat ttctaactgt tgttgttgct ctgcgaatca caaatgtat cagaatttct     900 ttcaatcagt atcccattga gtttcccatg gaattatttc tgattattgg cttcactgtg    960
attgcaaaca agataagcat ggccacagaa accagccaga cgcttattga catgattcct    1020
tatagctttc tgcttcctgt aacaccagat ttcagccttc ttcccaagat aattttacaa    1080
gccttctcct tatctttggt gagctccttt ctgctcatat ttctgggcaa gaagattgcc    1140
agtcttcaca attacagtgt caattccaac caggatttaa tagccatcgg cctttgcaat    1200
gtcgtcagtt cattttcag atcttgtgtg tttactggtg ctattgctag gactattatc     1260
caggataaat ctggaggaag acaacagttt gcatctctgg taggcgcagg tgtgatgctg    1320
ctcctgatgg tgaagatggg acacttttc tacacactgc caaatgctgt gctggctggt     1380
attattctga gcaacgtcat tccctacctt gaaaccattt ctaacctacc agcctgtgg    1440 aggcaggacc aatatgactg tgctcttgg atgatgacat tctcatcttc aattttcctg    1500
ggactggaca ttggactaat tatctcagta gtttctgctt tcttcatcac cactgttcgt    1560
tcacacagag ctaagattct tctcctgggt caaatcccta acaccaacat ttatagaagc    1620
atcaatgatt atcgggagat catcaccatt cctggggtga aaatcttcca gtgctgcagc    1680
tcaattacat ttgtaaatgt ttactaccta aagcataagc tgttaaaaga ggttgatatg    1740
gtaaaggtgc ctcttaaaga agaagaaatt ttcagcttgt ttaattcaag tgacaccaat    1800
ctacaaggag gaaagatttg caggtgtttc tgcaactgtg atgatctgga gccgctgccc    1860
aggattcttt acacagagcg atttgaaaat aaactggatc ccgaagcatc ctccattaac    1920
ctgattcact gctcacattt tgagagcatg aacacaagcc aaactgcatc cgaagaccaa    1980
gtgccataca cagtatcgtc cgtgtctcag aaaaatcaag gcaacagta tgaggaggtg     2040 gaggaagttt ggcttcctaa taactcatca agaaacagct caccaggact gcctgatgtg    2100
gcggaaagcc aggggaggag atcactcatc cctactcag atgcgtctct actgcccagt      2160
gtccacacca tcatcctgga tttctccatg gtacactacg tggattcacg ggggttagtc    2220
gtattaagac agatatgcaa tgcctttcaa aacgccaaca ttttgatact cattgcaggg    2280
tgtcactctt ccatagtcag ggcatttgag aggaatgatt tctttgacgc tggcatcacc    2340
aagacccagc tgttcctcag cgttcacgac gccgtgctgt tgccttgtc aaggaaggtc     2400 ataggctcct ctgagttaag catcgatgaa tccgagacag tgatacggga aacctactca    2460
gaaacagaca gaatgacaa ttcaagatat aaaatgagca gcagttttct aggaagccaa     2520
aaaaatgtaa gtccaggctt catcaagatc caacagcctg tagaagagga gtcggagttg    2580
gatttggagc tggaatcaga acaagaggct gggctgggtc tggacctaga cctggatcgg    2640
gagctggagc ctgaaatgga gcccaaggct gagaccgaga ccaagaccca gaccgagatg    2700
gagccccagc ctgagactga gcctgagatg gagcccaacc ccaaatctag gccaagagct    2760 cacactttc ctcagcagcg ttactggcct atgtatcatc cgtctatggc ttccacccag     2820
```

```
tctcagactc agactcggac atggtcagtg gagaggagac gccatcctat ggattcatac    2880
tcaccagagg gcaacagcaa tgaagatgtc tag                                 2913
```

<210> SEQ ID NO 7
<211> LENGTH: 970
<212> TYPE: PRT
<213> ORGANISM: homo sapiens
<220> FEATURE:
<221> NAME/KEY: VARIANT
<222> LOCATION: (1)...(970)
<223> OTHER INFORMATION: Xaa = Any Amino Acid

<400> SEQUENCE: 7

```
Met Ala Gln Leu Glu Arg Ser Ala Ile Ser Gly Phe Ser Ser Lys Ser
 1               5                  10                  15

Arg Arg Asn Ser Phe Ala Tyr Asp Val Lys Arg Glu Val Tyr Asn Glu
                20                  25                  30

Glu Thr Phe Gln Gln Glu His Lys Arg Lys Ala Ser Ser Ser Gly Asn
            35                  40                  45

Met Asn Ile Asn Ile Thr Thr Phe Arg His His Val Gln Cys Arg Cys
        50                  55                  60

Ser Trp His Arg Phe Leu Arg Cys Met Leu Thr Ile Phe Pro Phe Leu
65                  70                  75                  80

Glu Trp Met Cys Met Tyr Arg Leu Lys Asp Trp Leu Gly Asp Leu
                85                  90                  95

Leu Ala Gly Ile Ser Val Gly Leu Val Gln Val Pro Gln Gly Leu Thr
               100                 105                 110

Leu Ser Leu Leu Ala Arg Gln Leu Ile Pro Pro Leu Asn Ile Ala Tyr
            115                 120                 125

Ala Ala Phe Cys Ser Ser Val Ile Tyr Val Ile Phe Gly Ser Cys His
        130                 135                 140

Gln Met Ser Val Gly Ser Phe Leu Val Ser Ala Leu Leu Ile Asn
145                 150                 155                 160

Val Leu Lys Val Ser Pro Phe Asn Asn Gly Gln Leu Val Met Gly Ser
                165                 170                 175

Phe Val Lys Asn Glu Phe Ser Ala Pro Ser Tyr Leu Met Gly Tyr Asn
            180                 185                 190

Lys Ser Leu Ser Val Val Ala Thr Thr Thr Phe Leu Thr Gly Ile Ile
        195                 200                 205

Gln Leu Ile Met Gly Val Leu Gly Leu Gly Phe Ile Ala Thr Tyr Leu
    210                 215                 220

Pro Glu Ser Ala Met Asn Ala Tyr Leu Ala Ala Val Ala Leu His Ile
225                 230                 235                 240

Met Leu Ser Gln Leu Thr Phe Ile Phe Gly Ile Met Ile Ser Phe His
                245                 250                 255

Ala Gly Pro Ile Ser Phe Phe Tyr Asp Ile Ile Asn Tyr Cys Val Ala
            260                 265                 270

Leu Pro Lys Ala Asn Ser Thr Ser Ile Leu Val Phe Leu Thr Val Val
        275                 280                 285

Val Ala Leu Arg Ile Asn Lys Cys Ile Arg Ile Ser Phe Asn Gln Tyr
    290                 295                 300

Pro Ile Glu Phe Pro Met Glu Leu Phe Leu Ile Gly Phe Thr Val
305                 310                 315                 320

Ile Ala Asn Lys Ile Ser Met Ala Thr Glu Thr Ser Gln Thr Leu Ile
                325                 330                 335
```

```
Asp Met Ile Pro Tyr Ser Phe Leu Leu Pro Val Thr Pro Asp Phe Ser
            340                 345                 350
Leu Leu Pro Lys Ile Ile Leu Gln Ala Phe Ser Leu Ser Leu Val Ser
            355                 360                 365
Ser Phe Leu Leu Ile Phe Leu Gly Lys Lys Ile Ala Ser Leu His Asn
370                 375                 380
Tyr Ser Val Asn Ser Asn Gln Asp Leu Ile Ala Ile Gly Leu Cys Asn
385                 390                 395                 400
Val Val Ser Ser Phe Phe Arg Ser Cys Val Phe Thr Gly Ala Ile Ala
                405                 410                 415
Arg Thr Ile Ile Gln Asp Lys Ser Gly Gly Arg Gln Gln Phe Ala Ser
                420                 425                 430
Leu Val Gly Ala Gly Val Met Leu Leu Leu Met Val Lys Met Gly His
            435                 440                 445
Phe Phe Tyr Thr Leu Pro Asn Ala Val Leu Ala Gly Ile Ile Leu Ser
            450                 455                 460
Asn Val Ile Pro Tyr Leu Glu Thr Ile Ser Asn Leu Pro Ser Leu Trp
465                 470                 475                 480
Arg Gln Asp Gln Tyr Asp Cys Ala Leu Trp Met Met Thr Phe Ser Ser
                485                 490                 495
Ser Ile Phe Leu Gly Leu Asp Ile Gly Leu Ile Ile Ser Val Val Ser
            500                 505                 510
Ala Phe Phe Ile Thr Thr Val Arg Ser His Arg Ala Lys Ile Leu Leu
            515                 520                 525
Leu Gly Gln Ile Pro Asn Thr Asn Ile Tyr Arg Ser Ile Asn Asp Tyr
            530                 535                 540
Arg Glu Ile Ile Thr Ile Pro Gly Val Lys Ile Phe Gln Cys Cys Ser
545                 550                 555                 560
Ser Ile Thr Phe Val Asn Val Tyr Tyr Leu Lys His Lys Leu Leu Lys
                565                 570                 575
Glu Val Asp Met Val Lys Val Pro Leu Lys Glu Glu Ile Phe Ser
                580                 585                 590
Leu Phe Asn Ser Ser Asp Thr Asn Leu Gln Gly Gly Lys Ile Cys Arg
            595                 600                 605
Cys Phe Cys Asn Cys Asp Asp Leu Glu Pro Leu Pro Arg Ile Leu Tyr
610                 615                 620
Thr Glu Arg Phe Glu Asn Lys Leu Asp Pro Glu Ala Ser Ser Ile Asn
625                 630                 635                 640
Leu Ile His Cys Ser His Phe Glu Ser Met Asn Thr Ser Gln Thr Ala
                645                 650                 655
Ser Glu Asp Gln Val Pro Tyr Thr Val Ser Ser Val Ser Gln Lys Asn
                660                 665                 670
Gln Gly Gln Gln Tyr Glu Glu Val Glu Glu Val Trp Leu Pro Asn Asn
            675                 680                 685
Ser Ser Arg Asn Ser Ser Pro Gly Leu Pro Asp Val Ala Glu Ser Gln
690                 695                 700
Gly Arg Arg Ser Leu Ile Pro Tyr Ser Asp Ala Ser Leu Leu Pro Ser
705                 710                 715                 720
Val His Thr Ile Ile Leu Asp Phe Ser Met Val His Tyr Val Asp Ser
                725                 730                 735
Arg Gly Leu Val Val Leu Arg Gln Ile Cys Asn Ala Phe Gln Asn Ala
            740                 745                 750
Asn Ile Leu Ile Leu Ile Ala Gly Cys His Ser Ser Ile Val Arg Ala
            755                 760                 765
```

```
Phe Glu Arg Asn Asp Phe Phe Asp Ala Gly Ile Thr Lys Thr Gln Leu
        770                 775                 780

Phe Leu Ser Val His Asp Ala Val Leu Phe Ala Leu Ser Arg Lys Val
785                 790                 795                 800

Ile Gly Ser Ser Glu Leu Ser Ile Asp Glu Ser Glu Thr Val Ile Arg
                805                 810                 815

Glu Thr Tyr Ser Glu Thr Asp Lys Asn Asp Asn Ser Arg Tyr Lys Met
                820                 825                 830

Ser Ser Ser Phe Leu Gly Ser Gln Lys Asn Val Ser Pro Gly Phe Ile
                835                 840                 845

Lys Ile Gln Gln Pro Val Glu Glu Ser Glu Leu Asp Leu Glu Leu
    850                 855                 860

Glu Ser Glu Gln Glu Ala Gly Leu Gly Leu Asp Leu Asp Leu Asp Arg
865                 870                 875                 880

Glu Leu Glu Pro Glu Met Glu Pro Lys Ala Glu Thr Glu Thr Lys Thr
                885                 890                 895

Gln Thr Glu Met Glu Pro Gln Pro Glu Thr Glu Pro Glu Met Glu Pro
                900                 905                 910

Asn Pro Lys Ser Arg Pro Arg Ala His Thr Phe Pro Gln Gln Arg Tyr
                915                 920                 925

Trp Pro Met Tyr His Pro Ser Met Ala Ser Thr Gln Ser Gln Thr Gln
    930                 935                 940

Thr Arg Thr Trp Ser Val Glu Arg Arg His Pro Met Asp Ser Tyr
945                 950                 955                 960

Ser Pro Glu Gly Asn Ser Asn Glu Asp Val
                965                 970

<210> SEQ ID NO 8
<211> LENGTH: 3749
<212> TYPE: DNA
<213> ORGANISM: homo sapiens

<400> SEQUENCE: 8
ttttccaact ccccatctcc tccctcctca gattaaaaga agttatatgg actttgtgat      60
gttttctgcc gctttgtgaa gtaggcctta tttctcttgt cctttcgtac agggaggaat    120
ttgaagtaga tagaaaccga cctggattac tccggtctga actcagatca cgtaggactt    180
taatcgttga acaaacgaac ctttaatagc ggctgcacca tcgggatgtc ctgatccaac    240
atcgaggtcg taaaccctat tgttgatatg gactctagaa taggattgcg ctgttatccc    300
tagggtaact tgttccgttg gtcaagttat tggatcaatt gagtatagta gttcgctttg    360
actggtgaag tcttggcatg tactgctcgg aggttgggtt ctgctccgag gtcgcccaa     420 ccgaaatttt taatgcagga gcgcccgcac tcccgccccc gccaaggagc caggaatggc    480
acaactagag aggagcgcca tctctggctt cagctctaag tccaggcgaa actcattcgc    540
atatgatgtt aagcgtgaag tatacaatga ggagaccttt caacaggaac acaaaaggaa    600
ggcctcctct tctgggaaca tgaacatcaa catcaccacc ttcagacacc acgtccagtg    660
ccgctgctca tggcacaggt tcctacgatg crtgcttaca atctttccct tcctagaatg    720
gatgtgtatg tatcgattaa aggattggct tctgggagac ttacttgctg gtataagtgt    780
tggccttgtg caagttcccc aaggcctgac acttagtttg ctggcaaggc aactgattcc    840
tcctctcaac atcgcttatg cagctttctg ttcttcggta atctatgtaa tttttggatc    900
gtgtcatcaa atgtccgttg gttccttctt cctggtgagt gctctgctga tcaacgttct    960
```

```
gaaagtgagc ccattcaaca acggtcaact ggtcatggga tctttcgtca agaatgagtt    1020
ttcggccccc tcctacctta tgggctataa taaatccttg agtgtggtgg caaccacaac    1080
ttttctgact gggattattc agctaataat gggcgtattg ggtttgggct tcattgccac    1140
ttaccttccg gagtctgcaa tgaatgctta cctggctgct gtggcacttc atatcatgct    1200
gtcccagctg actttcatct tgggattat gattagtttc catgccggtc ccatctcctt    1260
cttctatgac ataattaatt actgtgtagc tctcccaaaa gcgaattcca ccagcattct    1320
agtatttcta actgttgttg ttgctctgcg aatcaacaaa tgtatcagaa tttctttcaa    1380
tcagtatccc attgagtttc ccatggaatt atttctgatt attggcttca ctgtgattgc    1440
aaacaagata agcatggcca cagaaaccag ccagacgctt attgacatga ttccttatag    1500
ctttctgctt cctgtaacac cagatttcag ccttcttccc aagataattt tacaagcctt    1560
ctccttatct ttggtgagct cctttctgct catatttctg gcaagaaga ttgccagtct    1620 tcacaattac agtgtcaatt ccaaccagga tttaatagcc atcggccttt gcaatgtcgt    1680
cagttcattt ttcagatctt gtgtgtttac tggtgctatt gctaggacta ttatccagga    1740
taaatctgga ggaagacaac agtttgcatc tctggtaggc gcaggtgtga tgctgctcct    1800
gatggtgaag atgggacact ttttctacac actgccaaat gctgtgctgg ctggtattat    1860
tctgagcaac gtcattccct accttgaaac catttctaac ctacccagcc tgtggaggca    1920
ggaccaatat gactgtgctc tttggatgat gacattctca tcttcaattt tcctgggact    1980
ggacattgga ctaattatct cagtagtttc tgctttcttc atcaccactg ttcgttcaca    2040
cagagctaag attcttctcc tgggtcaaat ccctaacacc aacatttata gaagcatcaa    2100
tgattatcgg gagatcatca ccattcctgg ggtgaaaatc ttccagtgct gcagctcaat    2160
tacatttgta aatgtttact acctaaagca taagctgtta aaagaggttg atatggtaaa    2220
ggtgcctctt aaagaagaag aaattttcag cttgtttaat tcaagtgaca ccaatctaca    2280
aggaggaaag atttgcaggt gtttctgcaa ctgtgatgat ctggagccgc tgcccaggat    2340
tctttacaca gagcgatttg aaaataaact ggatcccgaa gcatcctcca ttaacctgat    2400
tcactgctca cattttgaga gcatgaacac aagccaaact gcatccgaag accaagtgcc    2460
atacacagta tcgtccgtgt ctcagaaaaa tcaagggcaa cagtatgagg aggtggagga    2520
agtttggctt cctaataact catcaagaaa cagctcacca ggactgcctg atgtggcgga    2580
aagccagggg aggagatcac tcatccctta ctcagatgcg tctctactgc ccagtgtcca    2640
caccatcatc ctggatttct ccatggtaca ctacgtggat tcacgggggt tagtcgtatt    2700
aagacagata tgcaatgcct ttcaaaacgc caacattttg atactcattg cagggtgtca    2760
ctcttccata gtcagggcat ttgagaggaa tgatttcttt gacgctggca tcaccaagac    2820
ccagctgttc ctcagcgttc acgacgccgt gctgtttgcc ttgtcaagga aggtcatagg    2880
ctcctctgag ttaagcatcg atgaatccga cacagtgata cgggaaacct actcagaaac    2940
agacaagaat gacaattcaa gatataaaat gagcagcagt tttctaggaa gccaaaaaaa    3000
tgtaagtcca ggcttcatca agatccaaca gcctgtagaa gaggagtcgg agttggattt    3060
ggagctggaa tcagaacaag aggctgggct gggtctggac ctagacctgg atcgggagct    3120
ggagcctgaa atggagccca aggctgagac cgagaccaag acccagaccg agatggagcc    3180
ccagcctgag actgagcctg agatggagcc caaccccaaa tctaggccaa gagctcacac    3240
ttttcctcag cagcgttact ggcctatgta tcatccgtct atggcttcca cccagtctca    3300
```

-continued

| | |
|---|---|
| gactcagact cggacatggt cagtggagag gagacgccat cctatggatt catactcacc | 3360 |
| agagggcaac agcaatgaag atgtctagga gatgaactag aaataagggg tcagataatg | 3420 |
| ctggcaaatc ctcctaccca aaaagggtc aattgtccag agacctagac tggatacgaa | 3480 |
| ctagcagtac ttccttcctg actgtgactc ctactacctg ccagccttct tccttgctct | 3540 |
| gcgctgggat catactccca aatcacatta ctaaatgcca acaattatct ctgaattccc | 3600 |
| tatccaggct ccctcattt caccttcagc atatattcta gtcatgaatt ccttcttca | 3660 |
| cacacccac atctctgggc tttgtgccag accatctcta acttaatcct ctcatccctg | 3720 |
| ttcccctttc tccaaagaga tgaagctca | 3749 |

<210> SEQ ID NO 9
<211> LENGTH: 1524
<212> TYPE: DNA
<213> ORGANISM: homo sapiens

<400> SEQUENCE: 9

| | |
|---|---|
| atggggtgtt ggggtcggaa ccggggccgg ctgctgtgca tgctggcgct gaccttcatg | 60 |
| ttcatggtgc tggaggtggt ggtgagccgg gtgacctcgt cgctggcgat gctctccgac | 120 |
| tccttccaca tgctgtcgga cgtgctggcg ctggtggtgg cgctggtggc cgagcgcttc | 180 |
| gcccggcgga cccacgccac ccagaagaac acgttcggct ggatccgagc cgaggtaatg | 240 |
| ggggctctgg tgaacgccat cttcctgact ggctctgtt tcgccatcct gctggaggcc | 300 |
| atcgagcgct tcatcgagcc gcacgagatg cagcagccgc tggtggtcct tggggtcggc | 360 |
| gtggccgggc tgctggtcaa cgtgctgggg ctctgcctct ccaccatca cagcggcttc | 420 |
| agccaggact ccgccacgg ccactcgcac ggggtcacg gccacggcca cggcctcccc | 480 |
| aagggcctc gcgttaagag caccgcccc gggagcagcg acatcaacgt ggccccgggc | 540 |
| gagcagggtc ccgaccagga ggagaccaac accctggtgg ccaataccag caactccaac | 600 |
| gggctgaaat tggaccccgc agacccagaa aaccccagaa gtggtgatac agtggaagta | 660 |
| caagtgaatg gaaatcttgt cagagaacct gaccatatgg aactgaagaa agatagggct | 720 |
| ggacaactta acatgcgtgg agttttctg catgtccttg gagatgcctt gggttcagtg | 780 |
| attgtagtag taaatgcctt agtcttttac ttttcttgga aaggttgttc tgaaggggat | 840 |
| ttttgtgtga atccatgttt ccctgacccc tgcaaagcat ttgtagaaat aattaatagt | 900 |
| actcatgcat cactttatga ggctggtcct tgctgggtgc tatatttaga tccaactctt | 960 |
| tgtgttgtaa tggtttgtat acttcttac acaacctatc cattacttaa ggaatctgct | 1020 |
| cttattcttc tacaaactgt tcctaaacaa attgatatca gaaatttgat aaaagaactt | 1080 |
| cgaaatgttg aaggagttga ggaagttcat gaattacatg tttggcaact tgctggaagc | 1140 |
| agaatcattg ccactgctca cataaaatgt gaagatccaa catcatacat ggaggtggct | 1200 |
| aaaaccatta agacgttttt tcataatcac ggaattcacg ctactaccat tcagcctgaa | 1260 |
| tttgctagtg taggctctaa atcaagtgta gttccgtgtg aacttgcctg cagaacccag | 1320 |
| tgtgctttga agcaatgttg tgggacacta ccacaagccc cttatggaaa ggatgcagaa | 1380 |
| aagaccccag cagttagcat ttcttgttta gaacttagta acaatctaga gaagaagccc | 1440 |
| aggaggacta aagctgaaaa catccctgct gttgtgatag agattaaaaa catgccaaac | 1500 |
| aaacaacctg aatcatcttt gtga | 1524 |

<210> SEQ ID NO 10
<211> LENGTH: 507

```
<212> TYPE: PRT
<213> ORGANISM: homo sapiens

<400> SEQUENCE: 10

Met Gly Cys Trp Gly Arg Asn Arg Gly Arg Leu Leu Cys Met Leu Ala
 1               5                  10                  15

Leu Thr Phe Met Phe Met Val Leu Glu Val Val Ser Arg Val Thr
                20                  25                  30

Ser Ser Leu Ala Met Leu Ser Asp Ser Phe His Met Leu Ser Asp Val
                35                  40                  45

Leu Ala Leu Val Val Ala Leu Val Ala Glu Arg Phe Ala Arg Arg Thr
 50                  55                  60

His Ala Thr Gln Lys Asn Thr Phe Gly Trp Ile Arg Ala Glu Val Met
 65                  70                  75                  80

Gly Ala Leu Val Asn Ala Ile Phe Leu Thr Gly Leu Cys Phe Ala Ile
                85                  90                  95

Leu Leu Glu Ala Ile Glu Arg Phe Ile Glu Pro His Glu Met Gln Gln
                100                 105                 110

Pro Leu Val Val Leu Gly Val Gly Val Ala Gly Leu Leu Val Asn Val
                115                 120                 125

Leu Gly Leu Cys Leu Phe His His His Ser Gly Phe Ser Gln Asp Ser
130                 135                 140

Gly His Gly His Ser His Gly His Gly His Gly His Gly Leu Pro
145                 150                 155                 160

Lys Gly Pro Arg Val Lys Ser Thr Arg Pro Gly Ser Ser Asp Ile Asn
                165                 170                 175

Val Ala Pro Gly Glu Gln Gly Pro Asp Gln Glu Glu Thr Asn Thr Leu
                180                 185                 190

Val Ala Asn Thr Ser Asn Ser Asn Gly Leu Lys Leu Asp Pro Ala Asp
                195                 200                 205

Pro Glu Asn Pro Arg Ser Gly Asp Thr Val Glu Val Gln Val Asn Gly
                210                 215                 220

Asn Leu Val Arg Glu Pro Asp His Met Glu Leu Glu Asp Arg Ala
225                 230                 235                 240

Gly Gln Leu Asn Met Arg Gly Val Phe Leu His Val Leu Gly Asp Ala
                245                 250                 255

Leu Gly Ser Val Ile Val Val Asn Ala Leu Val Phe Tyr Phe Ser
                260                 265                 270

Trp Lys Gly Cys Ser Glu Gly Asp Phe Cys Val Asn Pro Cys Phe Pro
                275                 280                 285

Asp Pro Cys Lys Ala Phe Val Glu Ile Ile Asn Ser Thr His Ala Ser
                290                 295                 300

Leu Tyr Glu Ala Gly Pro Cys Trp Val Leu Tyr Leu Asp Pro Thr Leu
305                 310                 315                 320

Cys Val Val Met Val Cys Ile Leu Leu Tyr Thr Thr Tyr Pro Leu Leu
                325                 330                 335

Lys Glu Ser Ala Leu Ile Leu Leu Gln Thr Val Pro Lys Gln Ile Asp
                340                 345                 350

Ile Arg Asn Leu Ile Lys Glu Leu Arg Asn Val Glu Gly Val Glu Glu
                355                 360                 365

Val His Glu Leu His Val Trp Gln Leu Ala Gly Ser Arg Ile Ile Ala
                370                 375                 380

Thr Ala His Ile Lys Cys Glu Asp Pro Thr Ser Tyr Met Glu Val Ala
385                 390                 395                 400
```

```
Lys Thr Ile Lys Asp Val Phe His Asn His Gly Ile His Ala Thr Thr
                405                 410                 415

Ile Gln Pro Glu Phe Ala Ser Val Gly Ser Lys Ser Ser Val Val Pro
            420                 425                 430

Cys Glu Leu Ala Cys Arg Thr Gln Cys Ala Leu Lys Gln Cys Cys Gly
        435                 440                 445

Thr Leu Pro Gln Ala Pro Tyr Gly Lys Asp Ala Glu Lys Thr Pro Ala
    450                 455                 460

Val Ser Ile Ser Cys Leu Glu Leu Ser Asn Asn Leu Glu Lys Lys Pro
465                 470                 475                 480

Arg Arg Thr Lys Ala Glu Asn Ile Pro Ala Val Val Ile Glu Ile Lys
                485                 490                 495

Asn Met Pro Asn Lys Gln Pro Glu Ser Ser Leu
                500                 505
```

<210> SEQ ID NO 11
<211> LENGTH: 2222
<212> TYPE: DNA
<213> ORGANISM: homo sapiens

<400> SEQUENCE: 11

```
ctccggctgc ggctcttggt accccggctc cgggagccca gctccccgcc accgccgccg     60
cctgggtgtg ggggctgctg aggctgagcc gggcttcggc gccggctctg aggacggacg    120
cctgaggagc tgcgcggcgc ggcgccgccg gctggcggag aacgcccaca ggcgcggggc    180
tcggcggctt gacccgggct tgtccccgtg cggccgcggg ggcccctcag cggtttcccg    240
aacggcccga ctcgggcgct cctccgtgtc gcggtcgccg accctccgcg tcccgccaac    300
gccgccgctg caccagtctc cgggccgggc tcggcgggcc ccgcagccgc agccatgggg    360
tgttggggtc ggaaccgggg ccggctgctg tgcatgctgg cgctgacctt catgttcatg    420
gtgctggagg tggtggtgag ccgggtgacc tcgtcgctgg cgatgctctc cgactccttc    480
cacatgctgt cggacgtgct ggcgctggtg gtggcgctgg tggccgagcg cttcgcccgg    540
cggacccacg ccacccagaa gaacacgttc ggctggatcc gagccgaggt aatgggggct    600
ctggtgaacg ccatcttcct gactggcctc tgtttcgcca tcctgctgga ggccatcgag    660
cgcttcatcg agccgcacga gatgcagcag ccgctggtgg tccttggggt cggcgtggcc    720
gggctgctgg tcaacgtgct ggggctctgc ctcttccacc atcacagcgg cttcagccag    780
gactccggcc acggccactc gcacgggggt cacggccacg ccacggcct ccccaagggg    840
cctcgcgtta agagcacccg ccccgggagc agcgacatca acgtggcccc gggcgagcag    900
ggtcccgacc aggaggagac caacaccctg gtggccaata ccagcaactc caacgggctg    960
aaattggacc ccgcagaccc agaaaacccc agaagtggtg atacagtgga agtacaagtg   1020
aatggaaatc ttgtcagaga acctgaccat atggaactgg aagaagatag gctggacaa   1080
cttaacatgc gtggagtttt tctgcatgtc cttggagatg ccttgggttc agtgattgta   1140
gtagtaaatg ccttagtctt ttactttttct tggaaaggtt gttctgaagg ggattttttgt   1200
gtgaatccat gtttccctga cccctgcaaa gcatttgtag aaataattaa tagtactcat   1260
gcatcacttt atgaggctgg tccttgctgg gtgctatatt tagatccaac tctttgtgtt   1320
gtaatggttt gtatacttct ttacacaacc tatccattac ttaaggaatc tgctcttatt   1380
cttctacaaa ctgttcctaa acaaattgat atcagaaatt tgataaaaga acttcgaaat   1440
gttgaaggag ttgaggaagt tcatgaatta catgtttggc aacttgctgg aagcagaatc   1500
```

```
attgccactg ctcacataaa atgtgaagat ccaacatcat acatggaggt ggctaaaacc    1560
attaaagacg tttttcataa tcacggaatt cacgctacta ccattcagcc tgaatttgct    1620
agtgtaggct ctaaatcaag tgtagttccg tgtgaacttg cctgcagaac ccagtgtgct    1680
ttgaagcaat gttgtgggac actaccacaa gccccttatg gaaaggatgc agaaaagacc    1740
ccagcagtta gcatttcttg tttagaactt agtaacaatc tagagaagaa gcccaggagg    1800
actaaagctg aaaacatccc tgctgttgtg atagagatta aaaacatgcc aaacaaacaa    1860
cctgaatcat ctttgtgagt cttgaaaaag atgtgatatt tgacttttgc tttaaactgc    1920
aagaggaaaa agactccact gaaattctaa gtttgccaag tagtgtaatt gaagtccttg    1980
tctggtcaca cagtttaatt ctattttgt aagaacataa tgggactgca taacagagtt    2040
ctatattaca atttgtgatt attagtacag agtacagcta tgctgtgact gttttggaaa    2100
gccagtttta acactatgtt acatttttgt ttaaagtaag ttaaaccta tataacataa    2160 tgacatttga tttctggatt tttcccatgg ataaaaaatt aggggggata aaattaaaat    2220
tg                                                                  2222
```

HUMAN TRANSPORTER PROTEINS AND POLYNUCLEOTIDES ENCODING THE SAME

The present application claims the benefit of U.S. Provisional Application No. 60/185,956 which was filed on Feb. 29, 2000 and is herein incorporated by reference in its entirety.

INTRODUCTION

The present invention relates to the discovery, identification, and characterization of novel human polynucleotides encoding proteins that share sequence similarity with mammalian transporter proteins. The invention encompasses the described polynucleotides, host cell expression systems, the encoded proteins, fusion proteins, polypeptides and peptides, antibodies to the encoded proteins and peptides, and genetically engineered animals that either lack or over express the disclosed polynucleotides, antagonists and agonists of the proteins, and other compounds that modulate the expression or activity of the proteins encoded by the disclosed polynucleotides that can be used for diagnosis, drug screening, clinical trial monitoring, and treatment of diseases and disorders.

BACKGROUND OF THE INVENTION

Transporter proteins are integral membrane proteins that mediate or facilitate the passage of materials across the lipid bilayer. Given that the transport of materials across the membrane can play an important physiological role, transporter proteins are good drug targets. Additionally, one of the mechanisms of drug resistance involves diseased cells using cellular transporter systems to export chemotherapeutic agents from the cell. Such mechanisms are particularly relevant to cells manifesting resistance to a multiplicity of drugs.

SUMMARY OF THE INVENTION

The present invention relates to the discovery, identification, and characterization of nucleotides that encode novel human proteins, and the corresponding amino acid sequences of these proteins. The novel human proteins (NHPS) described for the first time herein share structural similarity with mammalian ion transporters, calcium transporters (particularly calcium transporting ATPases), sulfate transporters, and zinc transporters.

The novel human nucleic acid sequences described herein, encode alternative proteins/open reading frames (ORFS) of 1,177 and 374 amino acids in length (calcium-transporting ATPase, SEQ ID NOS: 2 and 4), 970 (sulfate transporter, SEQ ID NO:7), and 507 (zinc transporter, SEQ ID NO:10) amino acids in length.

The invention also encompasses agonists and antagonists of the described NHPs, including small molecules, large molecules, mutant NHPs, or portions thereof, that compete with native NHP, peptides, and antibodies, as well as nucleotide sequences that can be used to inhibit the expression of the described NHPs (e.g., antisense and ribozyme molecules, and gene or regulatory sequence replacement constructs) or to enhance the expression of the described NHP polynucleotides (e.g., expression constructs that place the described polynucleotide under the control of a strong promoter system), and transgenic animals that express a NHP transgene, or "knock-outs" (which can be conditional) that do not express a functional NHP. Knock-out mice can be produced in several ways, one of which involves the use of mouse embryonic stem cells ("ES cells") lines that contain gene trap mutations in a murine homolog of at least one of the described NHPs. When the unique NHP sequences described in SEQ ID NOS:1–11 are "knocked-out" they provide a method of identifying phenotypic expression of the particular gene as well as a method of assigning function to previously unknown genes. Additionally, the unique NHP sequences described in SEQ ID NOS:1–11 are useful for the identification of coding sequence and the mapping a unique gene to a particular chromosome.

Further, the present invention also relates to processes for identifying compounds that modulate, i.e., act as agonists or antagonists, of NHP expression and/or NHP activity that utilize purified preparations of the described NHPs and/or NHP product, or cells expressing the same. Such compounds can be used as therapeutic agents for the treatment of any of a wide variety of symptoms associated with biological disorders or imbalances.

DESCRIPTION OF THE SEQUENCE LISTING AND FIGURES

The Sequence Listing provides the sequences of the described NHP ORFs that encode the described NHP amino acid sequences. SEQ ID NOS 5, 8, and 11 describe nucleotides encoding NHP ORFs along with regions of flanking sequence.

DETAILED DESCRIPTION OF THE INVENTION

The NHPs described for the first time herein are novel proteins that may be expressed in, inter alia, human cell lines, fetal brain, pituitary, cerebellum, thymus, spleen, lymph node, bone marrow, trachea, kidney, fetal liver, liver, prostate, testis, thyroid, adrenal gland, salivary gland, stomach, small intestine, colon, adipose, rectum, pericardium, bone marrow, placenta, and gene trapped human cells. More particularly, the NHP that is similar to sulfate transporters (and the down-regulated in adenoma, or DRA, gene) is predominantly found in bone marrow and testis, and the zinc transporter-like NHP can be found expressed in the placenta.

The present invention encompasses the nucleotides presented in the Sequence Listing, host cells expressing such nucleotides, the expression products of such nucleotides, and: (a) nucleotides that encode mammalian homologs of the described polynucleotides, including the specifically described NHPs, and the NHP products; (b) nucleotides that encode one or more portions of the NHPs that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal (or hydrophobic transmembrane) sequence is deleted; (d) nucleotides that encode chimeric fusion proteins containing all or a portion of a coding region of an NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF) that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1xSSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of a DNA sequence that encodes and expresses an amino acid sequence presented in the Sequence Listing under moderately stringent conditions, e.g., washing in 0.2xSSC/0.1% SDS at 42° C. (Ausubel et al., 1989, supra), yet still encodes a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding NHP ORFs, or their functional equivalents, encoded by polynucleotide sequences that are about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. An oligonucleotide or polynucleotide sequence first disclosed in at least a portion of one or more of the sequences of SEQ ID NOS: 1–11 can be used as a hybridization probe in conjunction with a solid support matrix/substrate (resins, beads, membranes, plastics, polymers, metal or metallized substrates, crystalline or polycrystalline substrates, etc.). Of particular note are spatially addressable arrays (i.e., gene chips, microtiter plates, etc.) of oligonucleotides and polynucleotides, or corresponding oligopeptides and polypeptides, wherein at least one of the biopolymers present on the spatially addressable array comprises an oligonucleotide or polynucleotide sequence first disclosed in at least one of the sequences of SEQ ID NOS: 1–11, or an amino acid sequence encoded thereby. Methods for attaching biopolymers to, or synthesizing biopolymers on, solid support matrices, and conducting binding studies thereon are disclosed in, inter alia, U.S. Pat. Nos. 5,700,637, 5,556,752, 5,744,305, 4,631,211, 5,445,934, 5,252,743, 4,713,326, 5,424,186, and 4,689,405 the disclosures of which are herein incorporated by reference in their entirety.

Addressable arrays comprising sequences first disclosed in SEQ ID NOS:1–11 can be used to identify and characterize the temporal and tissue specific expression of a gene. These addressable arrays incorporate oligonucleotide sequences of sufficient length to confer the required specificity, yet be within the limitations of the production technology. The length of these probes is within a range of between about 8 to about 2000 nucleotides. Preferably the probes consist of 60 nucleotides and more preferably 25 nucleotides from the sequences first disclosed in SEQ ID NOS:1–11.

For example, a series of the described oligonucleotide sequences, or the complements thereof, can be used in chip format to represent all or a portion of the described sequences. The oligonucleotides, typically between about 16 to about 40 (or any whole number within the stated range) nucleotides in length can partially overlap each other and/or the sequence may be represented using oligonucleotides that do not overlap. Accordingly, the described polynucleotide sequences shall typically comprise at least about two or three distinct oligonucleotide sequences of at least about 8 nucleotides in length that are each first disclosed in the described Sequence Listing. Such oligonucleotide sequences can begin at any nucleotide present within a sequence in the Sequence Listing and proceed in either a sense (5'-to-3') orientation vis-a-vis the described sequence or in an antisense orientation.

Microarray-based analysis allows the discovery of broad patterns of genetic activity, providing new understanding of gene functions and generating novel and unexpected insight into transcriptional processes and biological mechanisms. The use of addressable arrays comprising sequences first disclosed in SEQ ID NOS:1–11 provides detailed information about transcriptional changes involved in a specific pathway, potentially leading to the identification of novel components or gene functions that manifest themselves as novel phenotypes.

Probes consisting of sequences first disclosed in SEQ ID NOS:1–11 can also be used in the identification, selection and validation of novel molecular targets for drug discovery. The use of these unique sequences permits the direct confirmation of drug targets and recognition of drug dependent changes in gene expression that are modulated through pathways distinct from the drugs intended target. These unique sequences therefore also have utility in defining and monitoring both drug action and toxicity.

As an example of utility, the sequences first disclosed in SEQ ID NOS:1–11 can be utilized in microarrays or other assay formats, to screen collections of genetic material from patients who have a particular medical condition. These investigations can also be carried out using the sequences first disclosed in SEQ ID NOS:1–11 in silico and by comparing previously collected genetic databases and the disclosed sequences using computer software known to those in the art.

Thus the sequences first disclosed in SEQ ID NOS:1–11 can be used to identify mutations associated with a particular disease and also as a diagnostic or prognostic assay.

Although the presently described sequences have been specifically described using nucleotide sequence, it should be appreciated that each of the sequences can uniquely be described using any of a wide variety of additional structural attributes, or combinations thereof. For example, a given sequence can be described by the net composition of the nucleotides present within a given region of the sequence in conjunction with the presence of one or more specific oligonucleotide sequence(s) first disclosed in the SEQ ID NOS: 1–11. Alternatively, a restriction map specifying the relative positions of restriction endonuclease digestion sites, or various palindromic or other specific oligonucleotide sequences can be used to structurally describe a given sequence. Such restriction maps, which are typically generated by widely available computer programs (e.g., the University of Wisconsin GCG sequence analysis package, SEQUENCHER 3.0, Gene Codes Corp., Ann Arbor, Mich., etc.), can optionally be used in conjunction with one or more discrete nucleotide sequence(s) present in the sequence that can be described by the relative position of the sequence relatve to one or more additional sequence(s) or one or more restriction sites present in the disclosed sequence.

For oligonucleotide probes, highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP gene homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of MRNA prepared from human or non-human cell lines or tissue known or suspected to express an allele of a NHP gene.

The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against a normal NHP product, as described below. (For screening techniques, see, for example, Harlow, E. and Lane, eds., 1988, "Antibodies: A Laboratory Manual", Cold Spring Harbor Press, Cold Spring Harbor, N.Y.).

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to a NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869,336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of the NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHP proteins or peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for an NHP, but can also identify compounds that trigger NHP-mediated activities or pathways.

Finally, the NHP products can be used as therapeutics. For example, soluble derivatives such as NHP peptides/domains corresponding to NHPs, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics the NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHPs, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

The NHP Sequences

The cDNA sequences and the corresponding deduced amino acid sequences of the described NHPs are presented in the Sequence Listing. The NHP nucleotides were obtained from clustered human gene trapped sequences, testis and mammary transcript RACE products, ESTs, and human brain, testis, trachea, pituitary, thymus, and mammary gland cDNA libraries (Edge Biosystems, Gaithersburg, Md.).

SEQ ID NOS:1–5 describe sequences that are similar to eucaryotic ATP-driven ion pumps such as calcium transporting ATPases, and which can be found expressed in a variety of human cells and tissues. The described sequences were assembled using gene trapped sequences and clones isolated from human kidney, lymph node, and thymus cDNA libraries (Edge Biosystems, Gaithersburg, Md.).

SEQ ID NOS:6–8 describe sequences that are similar to, inter alia, sulfate transporter and cotransporter proteins, and can be found expressed in human bone marrow and testis. Several polymorphisms were found in this NHP including, but not limited to, possible A-to-G transitions at nucleotide positions corresponding to nucleotides 589, 692, 917, 1,164, and 2,390 of, for example SEQ ID NO:8 which be silent or can result in the met corresponding to amino acid position 73 of SEQ ID NO:7 converting to a val (e.g., met 73 converting to val 73), val 148 converting to ile, asn 230 converting to lys, ile 562 converting to val. An additional C-to-T transition was identified that converts ala 777 to val. SEQ ID NOS:6–8 can be expressed in bone marrow and predominantly in testis cells. These NHPs were assembled from gene trapped sequences and clones from a human testis cDNA library (Edge Biosystems, Gaithersburg, Md.).

SEQ ID NOS:9–11 describe sequences that are similar to zinc transporters and vesicular transporters, can be found expressed in, inter alia, placenta and adrenal gland, and these NHP sequences were assembled using gene trapped sequences and clones from human adrenal and placenta cDNA libraries (Edge Biosystems, Gaithersburg, Md.).

Transporters and transporter related multidrug resistance (MDR) sequences, as well as uses and applications that are germane to the described NHPs, are described in U.S. Pat. Nos. 5,198,344 and 5,866,699 which are herein incorporated by reference in their entirety.

NHPS and NHP Polypeptides

NHPs, polypeptides, peptide fragments, mutated, truncated, or deleted forms of the NHPs, and/or NHP fusion proteins can be prepared for a variety of uses. These uses include but are not limited to the generation of antibodies, as reagents in diagnostic assays, the identification of other cellular gene products related to a NHP, as reagents in assays for screening for compounds that can be as pharmaceutical reagents useful in the therapeutic treatment of mental, biological, or medical disorders and diseases. Given the similarity information and expression data, the described NHPs can be targeted (by drugs, oligos, antibodies, etc,) in order to treat disease, or to therapeutically augment the efficacy of, for example, chemotherapeutic agents used in the treatment of breast or prostate cancer.

The Sequence Listing discloses the amino acid sequences encoded by the described NHP polynucleotides. The NHPs typically display have initiator methionines in DNA sequence contexts consistent with a translation initiation site.

The NHP amino acid sequences of the invention include the amino acid sequence presented in the Sequence Listing as well as analogues and derivatives thereof. Further, corresponding NHP homologues from other species are encompassed by the invention. In fact, any NHP protein encoded by the NHP nucleotide sequences described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is genericly representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, the NHP peptide or polypeptide is thought to be membrane protein, the hydrophobic regions of the protein can be excised and the resulting soluble peptide or polypeptide can be recovered from the culture media. Such expression systems also encompass engineered host cells that express a NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of the NHP, but to assess biological activity, e.g., in drug screening assays.

The expression systems that may be used for purposes of the invention include but are not limited to microorganisms such as bacteria (e.g., E. coli, B. subtilis) transformed with recombinant bacteriophage DNA, plasmid DNA or cosmid DNA expression vectors containing NHP nucleotide sequences; yeast (e.g., Saccharomyces, Pichia) transformed with recombinant yeast expression vectors containing NHP nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of or containing NHP, or for raising antibodies to a NHP, vectors that direct the expression of high levels of fusion protein products that are readily purified may be desirable. Such vectors include, but are not limited, to the E. coli expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign genes. The virus grows in *Spodoptera frugiperda* cells. A NHP coding sequence may be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted sequence is expressed (e.g., see Smith et al., 1983, J. Virol. 46:584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP gene or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the NHP product. Such engineered cell lines may be particularly useful in screening and evaluation of compounds that affect the endogenous activity of the NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk−, hgprt− or aprt− cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$.nitriloacetic acid-agarose columns and histidine-tagged proteins are selectively eluted with imidazole-containing buffers.

Also encompassed by the present invention are fusion proteins that direct the NHP to a target organ and/or facilitate transport across the membrane into the cytosol. Conjugation of NHPs to antibody molecules or their Fab fragments could be used to target cells bearing a particular epitope. Attaching the appropriate signal sequence to the NHP would also transport the NHP to the desired location within the cell. Alternatively targeting of NHP or its nucleic acid sequence might be achieved using liposome or lipid complex based delivery systems. Such technologies are described in *Liposomes:A Practical Approach,* New,RRC ed., Oxford University Press, New York and in U.S. Pat. Nos. 4,594,595, 5,459,127, 5,948,767 and 6,110,490 and their respective disclosures which are herein incorporated by reference in their entirety. Additionally embodied are novel protein constructs engineered in such a way that they facilitate transport of the NHP to the target site or desired organ. This goal may be achieved by coupling of the NHP to a cytokine or other ligand that provides targeting specificity, and/or to a protein transducing domain (see generally U.S. application Ser. Nos. 60/111,701 and 60/056,713, both of which are herein incorporated by reference, for examples of such transducing sequences) to facilitate passage across cellular membranes if needed and can optionally be engineered to include nuclear localization sequences when desired.

Anitbodies to NHP Products

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above.

The antibodies of the invention may be used, for example, in the detection of NHP in a biological sample and may, therefore, be utilized as part of a diagnostic or prognostic technique whereby patients may be tested for abnormal amounts of NHP. Such antibodies may also be utilized in conjunction with, for example, compound screening schemes for the evaluation of the effect of test compounds on expression and/or activity of a NHP gene product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of an NHP), truncated NHP polypeptides (NHP in which one or more domains have been deleted), functional equivalents of the NHP or mutated variant of the NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum.* Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. Such technologies are described in U.S. Pat. Nos. 6,075,181 and 5,877,397 and their respective disclosures which are herein incorporated by reference in their entirety. Also encompassed by the present invention is the use of fully humanized monoclonal antibodies as described in U.S. Pat. No. 6,150, 584 and respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP gene products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic" the NHP and, therefore, bind and activate or neutralize a receptor. Such anti-idiotypic antibodies or Fab fragments of such anti-idiotypes can be used in therapeutic regimens involving a NHP mediated pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising a sequence that:
   (a) encodes the amino acid sequence shown in SEQ ID NO: 7; and
   (b) hybridizes under highly stringent conditions with wash conditions of 0.1×SSC/0.1%SDS at 68° C. to the nucleotide sequence of SEQ ID NO: 6 or the complement thereof.

2. An isolated nucleic acid molecule comprising a nucleotide sequence that encodes the amino acid sequence shown in SEQ ID NO:7.

3. A recombinant expression vector comprising the isolated nucleic acid molecule of claim 2.

4. A host cell comprising the recombinant expression vector of claim 3.

* * * * *